(12) United States Patent
Clark et al.

(10) Patent No.: US 6,284,237 B1
(45) Date of Patent: Sep. 4, 2001

(54) METHODS OF TREATMENT USING IL-6

(76) Inventors: Steven C. Clark, 122 Johnson Rd., Winchester, MA (US) 01890; Gordon G. Wong, 239 Clark Rd., Brookline, MA (US) 02147; Paul Schendel, 39 Jeffrey Rd., Wayland, MA (US) 01778; John McCoy, 63 Pine Ridge Rd., Reading, MA (US) 01876

( * ) Notice: Subject to any disclaimer, the term of this patent is extended or adjusted under 35 U.S.C. 154(b) by 0 days.

This patent is subject to a terminal disclaimer.

(21) Appl. No.: 08/224,985

(22) Filed: Apr. 6, 1994

Related U.S. Application Data (60) Continuation of application No. 08/881,009, filed on May 8, 1992, now abandoned, which is a division of application No. 08/704,578, filed on Jun. 17, 1991, which is a division of application No. 08/124,745, filed on Nov. 24, 1987, now abandoned, which is a continuation-in-part of application No. 08/047,957, filed on May 8, 1987, now abandoned, which is a continuation-in-part of application No. 08/885,905, filed on Jul. 15, 1986, now abandoned, which is a continuation-in-part of application No. 08/883,207, filed on Jul. 8, 1986, now abandoned.

(30) Foreign Application Priority Data

Jul. 7, 1987 (WO) .................. PCT/US87/01611

(51) Int. Cl.[7] .................................................. A61K 38/20
(52) U.S. Cl. .................. 424/85.2; 424/184.1; 424/198.1; 514/2; 514/8; 514/885; 514/12; 435/69.52
(58) Field of Search ...................... 514/2, 8, 885, 514/12; 435/69.1, 69.52; 424/85.2, 184.1, 198.1

(56) References Cited

U.S. PATENT DOCUMENTS

| | | | |
|---|---|---|---|
| 4,675,285 | * 6/1987 | Clark et al. .............................. 435/6 |
| 5,087,448 | 2/1992 | Burstein .............................. 424/85.2 |
| 5,126,325 | 6/1992 | Kishimoto .............................. 514/12 |
| 5,178,856 | 1/1993 | Burstein .............................. 424/85.2 |
| 5,188,828 | 2/1993 | Goldberg .............................. 424/85.3 |
| 5,541,088 | 7/1996 | Kishimoto et al. .............. 435/69.52 |

FOREIGN PATENT DOCUMENTS

| | | |
|---|---|---|
| 0220574 | 5/1987 | (EP) . |
| 0 257 406 | 3/1988 | (EP) . |
| 0 356 180 | 2/1990 | (EP) . |
| 0 363 083 | 4/1990 | (EP) . |
| 0 378 171 | 7/1990 | (EP) . |
| 2063882 | 6/1981 | (GB) . |
| 861140699 | 11/1986 | (IL) . |
| 61115025A | 6/1986 | (JP) . |
| 61-246197 | 11/1986 | (JP) . |

OTHER PUBLICATIONS

J. Content et al., PNAS 79:2768–2772 (1982).

J. Content et al., Eur. J. Biochem. 152:253–257 (1985).

T. Hirano et al., J. Immunology 133:798 (1984).

T. Hirano et al., PNAS, 82:5490–5494 (1985).

H. Kikutani et al., J. Immunology 134:990 (1985).

A. Zilberstein et al., in The Interferon System, Serono Symposis, vol. 24:73–83 (G. B. Rossi & E., Dianzani eds.) New York:Raven Press 1985.

(List continued on next page.)

*Primary Examiner*—John Ulm
*Assistant Examiner*—Prema Mertz
(74) *Attorney, Agent, or Firm*—Scott A. Brown; Suzanne A. Sprunger; Thomas J. DesRosier (57) ABSTRACT

IL-6 is produced via recombinant DNA techniques. The peptide is useful in the treatment of disorders characterized by deficiencies in hematopoietic cells and in combination with other hematopoietins in cancer therapies.

8 Claims, 6 Drawing Sheets

OTHER PUBLICATIONS

T. Kishimoto, Annu.Rev. Immunology 3:133 (1985).
M. Kohase et al., Cell 45:659–666 (1986).
A. D. Sagar et al., J. Exp.Med. 156:744 (1982).
P. B. Sehgal et al., Nature (London) 288:95 (1980).
J. Weissenbach et al. PNAS 77:7152–7156 (1980).
Grantham et al., Nucl. Acids Res. 8(9):1893–1912 (1980).
Zilberstein et al., EMBO J. 5:2529–2537 (1986).
A. Billiau, Nature 324:415 (1986).
G. Haegeman et al., Bur. J. Biochem. 159:625–632 (1986).
T. Hirano et al., Nature (London) 324:73 (1986).
M. Revel et al., in The Biology of the Interferon System 1985 (eds. W. E. Stewart & H. Schellekens) 207–216; 119–124 Elsevier Amsterdam (1986).
M. Revel et al., Nature 325:581 (1987).
P. B. Seghal et al., PNAS 83:5219 (1986).
Kitahara, M. et al., J. Cancer Res.81:1032–1038 (1990).
Maekawa, T. et al., Int. J. Cancer 45:353–358 (1990).
Kimura et al., Eur. J. Immunol. 20:1927–1931 (1990).
Zilberstein, A. et al., EMBO J. 5:2529–2537 (1986).
Billiau, A., Nature 324:415 (1986).
Haegeman et al., Bur. J. Biochem. 159:625–632 (1986).
Hirano, T. et al., Nature (London) 324:73 (1986).
Revel, M. et al., in *The Biology of the Interferon System 1985* (eds. W. E. Stewart & H. Schellekens) 207–216; 119–124 Elsevier Amsterdam (1986).
Revel, M. et al., Nature 325:581 (1987).
Seghal, P. et al., Proc. Natl, Acad. Sci. 83:5219 (1986).
Seghal, P. et al., Science 235:731 (1987).
Takai, Y. et al, J. Immunol. 137:3494–3500 (1986).
Van Damme, J. et al., J. Exp. Med. 165:914 (1987).
Mayer, P. et al., Exp.Hematol. 19:688–696 (1991).
Takatsuki, et al., Cancer Research 50:2885–2890 (1990).
Asano, S. et al., Blood 75(8):1602–1605 (1990).
Ishibashi, T. et al., Blood 74(4):1241–1244 (1989).
Vieira et al Gene 087,9 259–268 (1982).*
Talmadge et al. Gene vol. 12 pp. 235–241 (1980).*
Rosenberg et al. in Methods in Entynology vol. 101, Academic Press, NY. pp. 123–138 (1983).*
Maxain & Gilbert in Methods in Enzynology vol. 65 Academic Press, NY. pp. 499–560 (1980).*
Okano, A. et al., Transplantation 48:495–498 (1989).
Suzuki, C. et al., Biochem.& Boiphys.Res.Comm. 159:933–938 (1989).
Okano, A. et al., Transplantation 47:738–740 (1989).
Herodin, F. et al., Blood 80:688–695 (1992).
Weissenbach, J. et al., Proc. Natl. Acad. Sci. U.S.A. 77:7152–7156 (1980).
Sehgal, P. et al., Nature 288:95–97 (1980).
Sagar, A. et al., J. Exp. Med. 156:744–755 (1982).
Content, J. et al., Proc. Natl. Acad. Sci. U.S.A. 79:2768–2772 (1982).
Content, J. et al., Eur. J. Biochem. 152:253–257 (1985).
Hirano, T. et al., J. Immunology 133:798–802 (1984).
Hirano, T. et al., Proc. Natl. Acad. Sci. U.S.A. 82:5490–5494 (1985).
Zilberstein, A. et al., *The Interferon System, Serono Symposia, vol. 24*: Kikutani, H. et al., J. Immunology 134:990–995 (1985).
Kishimoto, T., Ann. Rev. Immunology 3:133–157 (1985).
Kohase, M. et al., Cell 45:659–666 (1986).
Mule, J. et al., J. Exp. Med. 171:629–636 (1990).
Patchen, M. et al., Blood 77:472–480 (1991).
Kitahara, M. et al., J. Cancer Res. 81:1032–1038 (1990).
Maekawa, T. et al., Int. J. Cancer 45:353–358 (1990).
Hirano et al 1986 vol. 324 p. 73–76 Nature.*
Zilberstein et al 1986 vol. 5 No. 10 pp. 2529–2537 EMBO.*
Treuner et al 1983 The Biology of the interferon system 1983 pp. 551–518.*
Chirigos et al 1973 J. Nat.Can.Inst. 51, 1367–1368.*

* cited by examiner

FIG. 1A

```
       10         20         30         40         50
GAATTCCGGG AACGAAAGAG AAGCTCTATC TCCCCTCCAG GAGCCCAGCT ATG AAC TCC TTC
                                                      MET Asn Ser Phe
 65              80              95                  110
TCC ACA AGC GCC TTC GGT CCA GTT GCC TTC TCC CTG GGG CTG CTC CTG GTG TTG
Ser Thr Ser Ala Phe Gly Pro Val Ala Phe Ser Leu Gly Leu Leu Leu Val Leu
                125             140             155                 170
CCT GCT GCC TTC CCT GCC CCA GTA CCC CCA GGA GAA GAT TCC AAA GAT GTA GCC
Pro Ala Ala Phe Pro Ala Pro Val Pro Pro Gly Glu Asp Ser Lys Asp Val Ala
            185             200             215
GCC CCA CAC AGA CAG CCA CTC ACC TCT TCA GAA CGA ATT GAC CAA AAG AAG
Ala Pro His Arg Gln Pro Leu Thr Ser Ser Glu Arg Ile Asp Gln Lys Lys
    230             245             260             275
TAC ATC CTC GAC GGC ATC TCA GCC CTG AGA AAG GAG ACA AAC AAG AGT AAC
Tyr Ile Leu Asp Gly Ile Ser Ala Leu Arg Lys Glu Thr Asn Lys Ser Asn
            290             305             320
ATG TGT GAA AGC AAA GAG GCA CTG GCA GAA AAC AAC CTG AAC CTT CCA AAG
MET Cys Glu Ser Lys Glu Ala Leu Ala Glu Asn Asn Leu Asn Leu Pro Lys
 335             350             365             380
ATG GCT GAA GAT AAA GAT GGA TGC TTC CAA TCT GGA TTC AAT GAG GAG ACT TGC CTG
MET Ala Glu Asp Lys Asp Gly Cys Phe Gln Ser Gly Phe Asn Glu Glu Thr Cys Leu
 395             410             425             440
ATC ATC ACT ACT GGT CTT TTG GAG TTT GAG GTA CTA GAG TAC CTC CAG
Ile Ile Thr Thr Gly Leu Leu Glu Phe Glu Val Leu Glu Tyr Leu Gln
GTG AAA                                         TAC CTC CAG
Val Lys                                         Tyr Leu Gln
            455             470             485
AAC AGA TTT GAG AGT AGT GAG GAA CAA GCC AGA GCT GTG CAG ATG AGT ACA AAA
Asn Arg Phe Glu Ser Ser Glu Glu Gln Ala Arg Ala Val Gln MET Ser Thr Lys
```

```
                                                                                        545
GTC CTG ATC CAG TTC CTG CAG AAA AAG GCA AAG AAT CTA GAT GCA ATA ACC ACC
Val Leu Ile Gln Phe Leu Gln Lys Lys Ala Lys Asn Leu Asp Ala Ile Thr Thr
                                  515              530                 590
CCT GAC CCA ACC ACA AAT GCC AGC CTG ACG AAG CTG CAG GCA CAG AAC CAG
Pro Asp Pro Thr Thr Asn Ala Ser Leu Thr Lys Leu Gln Ala Gln Asn Gln
         560                        575                              650
TGG CTG CAG GAC ATG ACA ACT CAT CTC ATT CTG CGC AGC TTT AAG GAG TTC CTG
Trp Leu Gln Asp MET Thr Thr His Leu Ile Leu Arg Ser Phe Lys Glu Phe Leu
   605                  620                 635
                                                                         716
CAG TCC AGC CTG AGG GCT CTT CGG CAA ATG TAGCCATGGGC ACCTCAGATT GTTGTTGTTA
Gln Ser Ser Leu Arg Ala Leu Arg Gln MET
       665                   680                696          706

726          736          746          756           766          776          786
ATGGGCATTC CTTCTTCTGG TCAGAAACCT GTCCACTGGG CACAGAACTT ATGTTGTTCT CTATGGAGAA 796          806          816          826           836          846          856
CTAAAAGTAT GAGCGTTAGG ACACTATTTT AATTATTTT  AATTTATTAA TATTTAAATA TGTGAAGCTG 866          876          886          896           906          916          926
AGTTAATTTA TGTAAGTCAT ATTTATATTT TTAAGAAGTA CCACTTGAAA CATTTTATGT ATTAGTTTTG 936          946          956          966           976          986          996
AAATAATAAT GGAAAGTGGC TATGCAGTTT GAATATCCTT TGTTTCAGAG CCAGATCATT TCTTGGAAAG 1006         1016         1026         1036          1046         1056         1066
TGTAGGCTTA CCTCAAATAA ATGGCTAACT TATACATATT TTTAAAGAAA TATTTATATT GTATTTATAT 1076         1086         1096         1106          1116         1126         1136
AATGTATAAA TGGTTTTTAT ACCAATAAAT GGCATTTTAA AAAATTCAAA AAAAAAAAAA AAAAAAAGAA

TTC
```

*FIG. 1B*

```
                                                        ATG
                                                        Met
(28)    140              155              170
GCT CCA GTA CCT CCA GGT GAA GAT TCT AAA GAT GTA GCC GCC CCA CAC
Ala Pro Val Pro Pro Gly Glu Asp Ser Lys Asp Val Ala Ala Pro His
            185              200              215
AGA CAG CCA CTC ACC TCT TCA GAA CGA ATT GAC CAA AAA CAA ATT CGG TAC
Arg Gln Pro Leu Thr Ser Ser Glu Arg Ile Asp Gln Lys Gln Ile Arg Tyr
230              245              260              275
ATC CTC GAC GGC ATC TCA GCC CTG AGA AAG GAG ACA TGT AAC AAG AGT
Ile Leu Asp Gly Ile Ser Ala Leu Arg Lys Glu Thr Cys Asn Lys Ser
            290              305              320
AAC ATG TGT GAA AGC AAA AGC GCA CTG GCA GAA AAC AAC CTG AAC
Asn MET Cys Glu Ser Lys Ser Ala Leu Ala Glu Asn Asn Leu Asn
        335             (100)           365
                         350
CTT CCA AAG ATG GCT GAA AAA GAT GGA TGC TTC CAA TCT GGA TTC AAT
Leu Pro Lys MET Ala Glu Lys Asp Gly Cys Phe Gln Ser Gly Phe Asn
        380              395              410
GAG GAG ACT TGC CTG GTT AAA ATC ACT GGT CTT TTG GAG TTT GAG
Glu Glu Thr Cys Leu Val Lys Ile Thr Gly Leu Leu Glu Phe Glu
```

*FIG. 2A*

```
425
GTA TAC CTA GAG TAC CTC CAG AAC AGA TTT GAG AGT GAG GAA CAA
Val Tyr Leu Glu Tyr Leu Gln Asn Arg Phe Glu Ser Glu Glu Gln
                                    455
470                              485                    515
GCC AGA GCT GTG CAG ATG AGT ACA AAA GTC CTG ATC CAG TTC CTG CAG
Ala Arg Ala Val Gln MET Ser Thr Lys Val Leu Ile Gln Phe Leu Gln
                        500
                                            545          560
AAA AAG GCA AAT CTA GAT GCA ATA ACC CCT GAC CCA GAC CCA ACC ACA
Lys Lys Ala Asn Leu Asp Ala Ile Thr Pro Asp Pro Asp Pro Thr Thr
        530

AAT GCC AGC CTG CTG ACG AAG CTG CAG GCA CAG AAC CAG TGG CTG CAG
Asn Ala Ser Leu Leu Thr Lys Leu Gln Ala Gln Asn Gln Trp Leu Gln
            575                     590                605

GAC ATG ACA ACT CAT CTC ATT CTC ATT CTG AGG GCT CTT CGC AGC TTT AAG GAG TTC CTG CAG
Asp MET Thr Thr His Leu Ile Leu Ile Leu Arg Ala Leu Arg Ser Phe Lys Glu Phe Leu Gln
        620                 635                 650(200)

TCC AGC CTG AGG GCT CTT CGC CAA ATG TAGCATGG
Ser Ser Leu Arg Ala Leu Arg Gln MET
665                 680 (211)
```

Sequence of the C_I857 Ser-48 Allele of the lambda C_I Gene

```
                                                              312                                                         339
ATG AGC ACA AAA AAG AAA CCA TTA ACA CAA GAG CAG CTT GAG GAC GCA CGT CGC
                                                              366                                                         393
CCT AAA GCA ATT TAT GAA AAA AAG ATG GGG GAT AAT GAA CTT GGC TTA TCC CAG GAA TCT
                                                              420                                                         447
GTC GCA GAC AAG ATG GGG ATG GGG TCA GGC GTT AGT GCT TTA TTT AAT GGC
                                                              474                                                         501
ATC AAT GCA TTA AAT GCT TAT AAC GCA TTG CTT ACA AAA ATT CTC AAA GTT
                                                              528                                                         555
AGC GTT GAA GAA TTT AGC CCT TCA GCC AGA GAA ATC TAC GAG ATG TAT GAA
                                                              582                                                         609
GCG GTT AGT ATG CAG CCG TCA CTT AGA AGT GAG TAT CCT GTT TTT TCT
                                                              636                                                         663
CAT GTT CAG GCA GGG ATG TTC TCA CCT AAG CTT AGA ACC TTT ACC AAA GGT GAT
                                                              690                                                         717
GCG GAG AGA TGG GTA AGC ACA ACC AAA GCC AGT GAT TCT GCA TTC TGG CTT
                                                              744                                                         771
GAG GTT GAA GGT AAT TCC ATG ACC GCA ACA GGC TCC AAG CCA AGC TTT CCT
                                                              798                                                         825
GAC GGA ATG TTA ATT CTC GTT GAC CCT GAG CAG GCT GTT GAG CCA GGT GAT TTC
                                                              852                                                         879
TGC ATA GCC AGA CTT GGG GGT GAT GAG TTT ACC TTC AAG AAA CTG ATC AGG GAT
                                                              906                                                         933
AGC GGT CAG GTG TTT TTA CAA CCA CCA AAC CCA CAG TAC CCA ATG ATC CCA TGC
                                                              960                                                         987
AAT GAG AGT TGT TCC GTT GTG GGG AAA GTT ATC GCT AGT CAG TGG CCT GAA GAG
ACG TTT GGC TGA
```

Figure 1A:
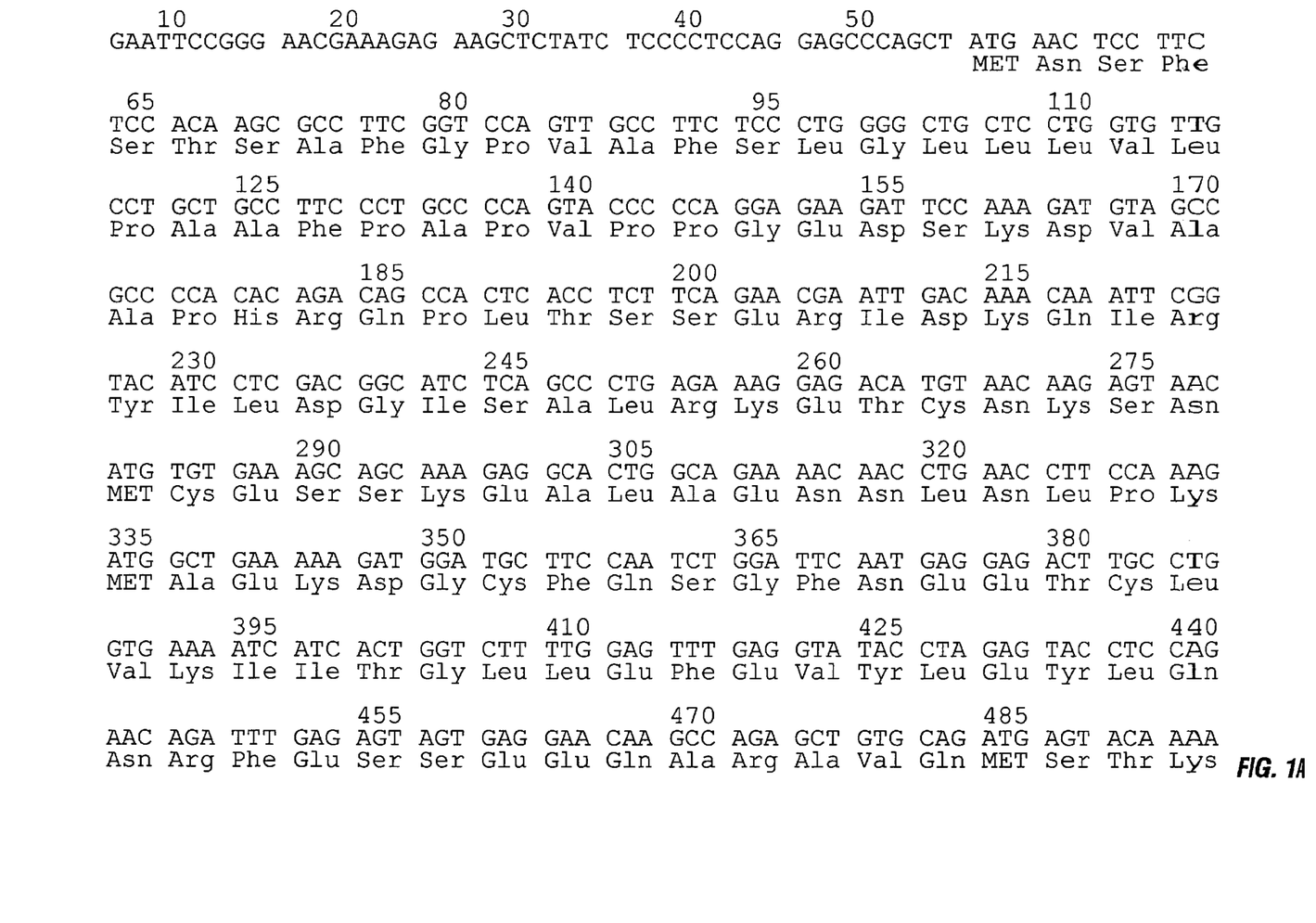
FIG. 1 illustrates the full cDNA and amino acid sequence of IL-6.
Figure 1B:
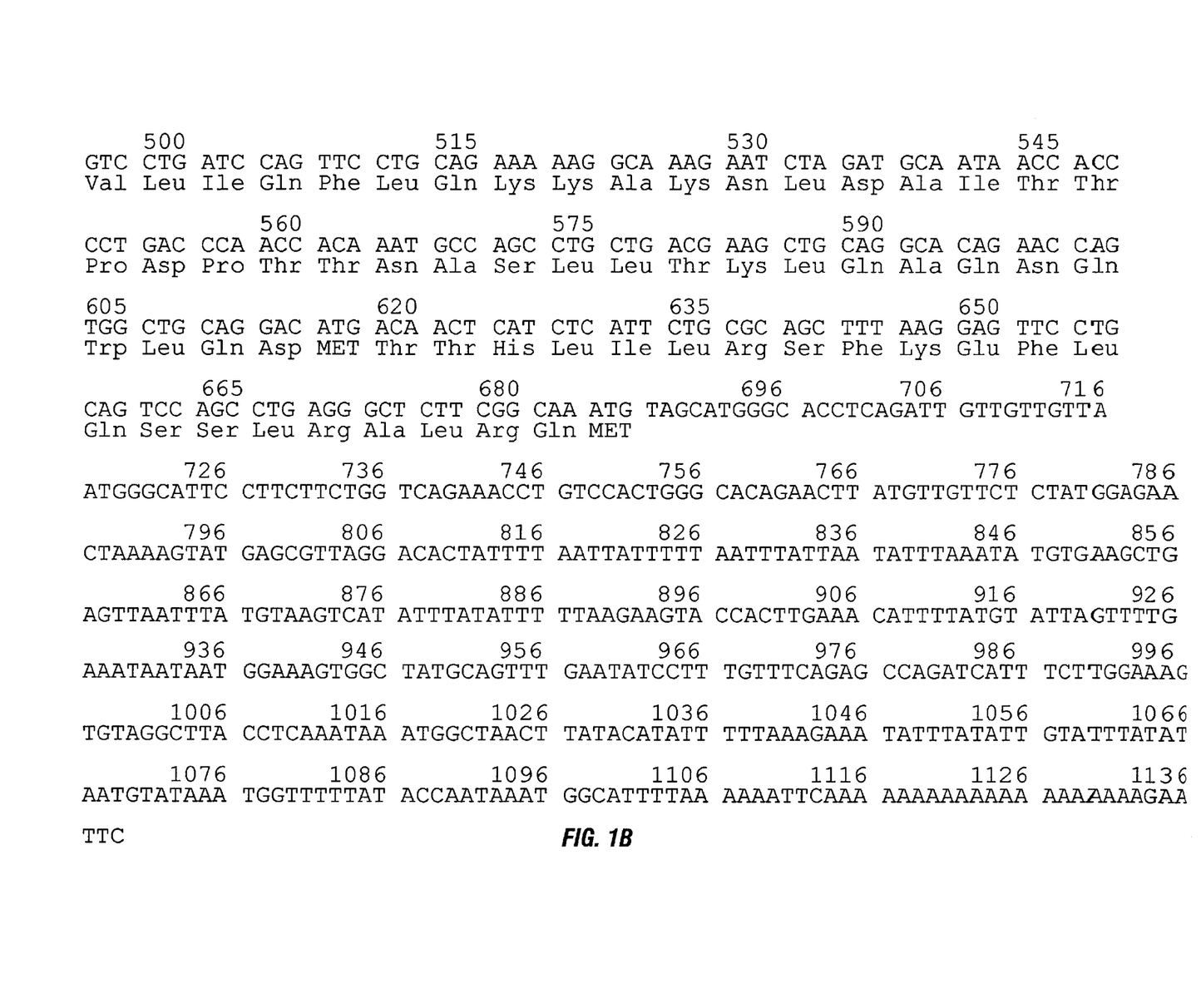

FIG. 4 ically the same sequence as that of amino acid #28 through amino acid #212 of FIG. 1. The cDNA sequence in this process is in operative association with an expression control sequence therefor. The process for producing IL-6 may also employ a cDNA sequence which is substantially the same as the complete nucleotide sequence of FIG. 1.

In another aspect, there is provided a process for producing non-glycoslyated IL-6. This process includes culturing a suitable bacterial cell transformed with a cDNA sequence encoding a protein characterized by containing a peptide sequence comprising substantially the same sequence as that of amino acid #28 through amino acid #211 of FIG. 2. The cDNA sequence employed in this process is also in operative association with a suitable expression control sequence.

In yet another aspect, the invention provides transformation vectors useful in the processes of the invention. These vectors contain DNA sequences the same or substantially the same as those of FIG. 1 or FIG. 2 under the control of suitable expression control sequences.

As still another aspect, the invention includes the human protein IL-6 substantially free from association with other proteins. IL-6 may be produced by either of the above-described processes, and may thus be a glycosylated protein or a non-glycosylated protein.

In a further aspect, there is provided a pharmaceutical composition comprising an effective amount of IL-6 according to the invention. The composition may further include an effective amount of at least one hematopoietin, interleukin, growth factor or antibody, most desirably either of the proteins IL-3 or IL-2. The therapeutic composition containing IL-6, particularly in combination with IL-2 and further in combination with gamma interferon, may be useful for the treatment of cancer.

The therapeutic compositions of the invention may be employed in treating human patients with diseases characterized by damaged immune system functions by administering to a patient an effective amount of the IL-6 peptide. This therapeutic method may further entail co-administering to a patient an effective amount of IL-2 or IL-3. In the treatment of cancers, the therapeutic method may further involve co-administering an effective amount of gamma interferon with IL-6 and IL-2. Other hematopoietins, growth factors or antibodies, as well as other conventional therapeutic agents may also be combined with IL-6.

Other aspects and advantages of the present invention will be apparent upon consideration of the following detailed description of the invention, including illustrative examples of the practice thereof.

METHODS OF TREATMENT USING IL-6

This is a continuation of U.S. application Ser. No. 881,009, filed May 8, 1992, now abandoned; which is a divisional application of U.S. application Ser. No. 704,578, filed Jun. 17, 1991; which is a divisional of U.S. application Ser. No. 124,745, filed Nov. 24, 1987 and now abandoned; which is a continuation-in-part of U.S. application Ser. Nos. 047,957 (filed May 8, 1987 as a CIP of 885,905 and now abandoned); 885,905 (filed Jul. 15, 1986 as a CIP of 883,207 and now abandoned); and 883,207 (filed Jul. 8, 1986 and now abandoned); and which also claims the benefit under 35 U.S.C. § 119 of the priority date of International application PCT/US87/01611, filed Jul. 7, 1987.

The present invention relates to the production of a recombinant IL-6 protein and novel methods for the use of this human protein which participates in immune regulation.

BACKGROUND OF THE INVENTION

Hematopoietins or hematopoietic growth factors are proteins that promote the survival, growth and differentiation of hematopoietic cells. The biochemical and biological identification and characterization of certain hematopoietins has been hampered by the small quantities of the factors available from natural sources, e.g., blood and urine. With recombinant genetic engineering techniques, however, some of these hematopoietins have been molecularly cloned, heterologously expressed and purified to homogeneity. Among these hematopoietins are colony stimulating factors (CSFs) characterized by the ability to support the growth in vitro of colonies of hematopoietic cells arising from progenitor cells of bone marrow, fetal liver and other organs, e.g. GM-CSF, G-CSF, CSF-1 and IL-3. [See, e.g., D. Metcalf, *Blood*, 67(2): 257–267 (1986); Y. C. Yang et al, *Cell*, 47(1):3–10 (1986); R. Donahue et al, *Nature*, 321:872–875 (1986)].

Subsequent to the filing date of the present inventors' United States priority applications, several publications issued by other researchers describing proteins characterized by other biological activities and names, which were identical to the novel protein, called IL-6 described herein and in the priority applications. See, Haegeman et al, *Eur. J. Biochem.*, 159:625–632 (1986) and references cited therein [the 26 kd protein inducible in human fibroblasts]; Zilberstein et al, *EMBO J.*, 5:2529–2537 (1986) [IFN-beta-2 with weak interferon activity]; and Hirano et al, *Nature*, 324:73–76 (1986) [BCDF or BSF-2 for its B cell stimulatory activity]. See also, published European Patent Application 220,574. Several of these papers reported purification of the natural substance.

BRIEF SUMMARY OF THE INVENTION

In one aspect, the invention discloses a process for producing IL-6 comprising culturing a suitable cell transformed with a CDNA sequence encoding a protein charac-

DETAILED DESCRIPTION OF THE INVENTION

The present invention provides a method for producing human IL-6 substantially free from association with other human proteins. The preparative method of the invention involves culturing a host cell transformed with a DNA sequence encoding for the IL-6 protein, which is under the control of suitable expression control sequences. The DNA sequence encoding the IL-6 protein contains the same nucleotide sequence or substantially the same nucleotide sequence as nucleotide #132 through nucleotide #689, or nucleotide #51 through nucleotide #1139, as depicted in FIG. 1. One cDNA sequence for use in this method includes the complete nucleotide sequence of FIG. 1. The approximately 1.1 kb DNA sequence of FIG. 1 is harbored in plasmid pCSF309 in *E. coli* MC1061, which was deposited in the American Type Culture Collection, 12301 Parklawn Dr., Rockville, Md. on Jul. 11, 1986 and given accession number ATCC 67153.

Figure 2A:
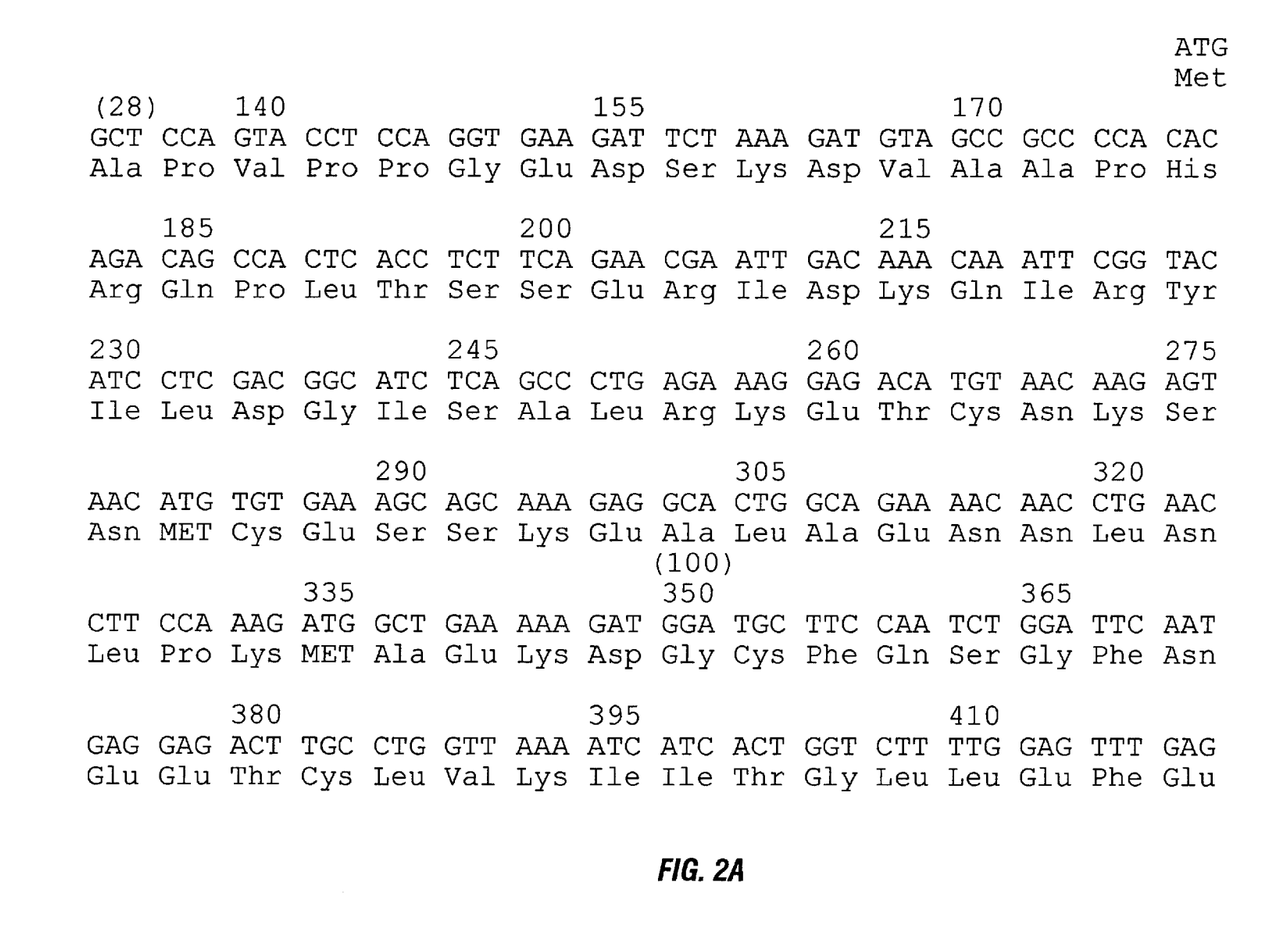
FIG. 2 illustrates a modified cDNA sequence particularly suitable for bacterial expression of IL-6.
Figure 2B:
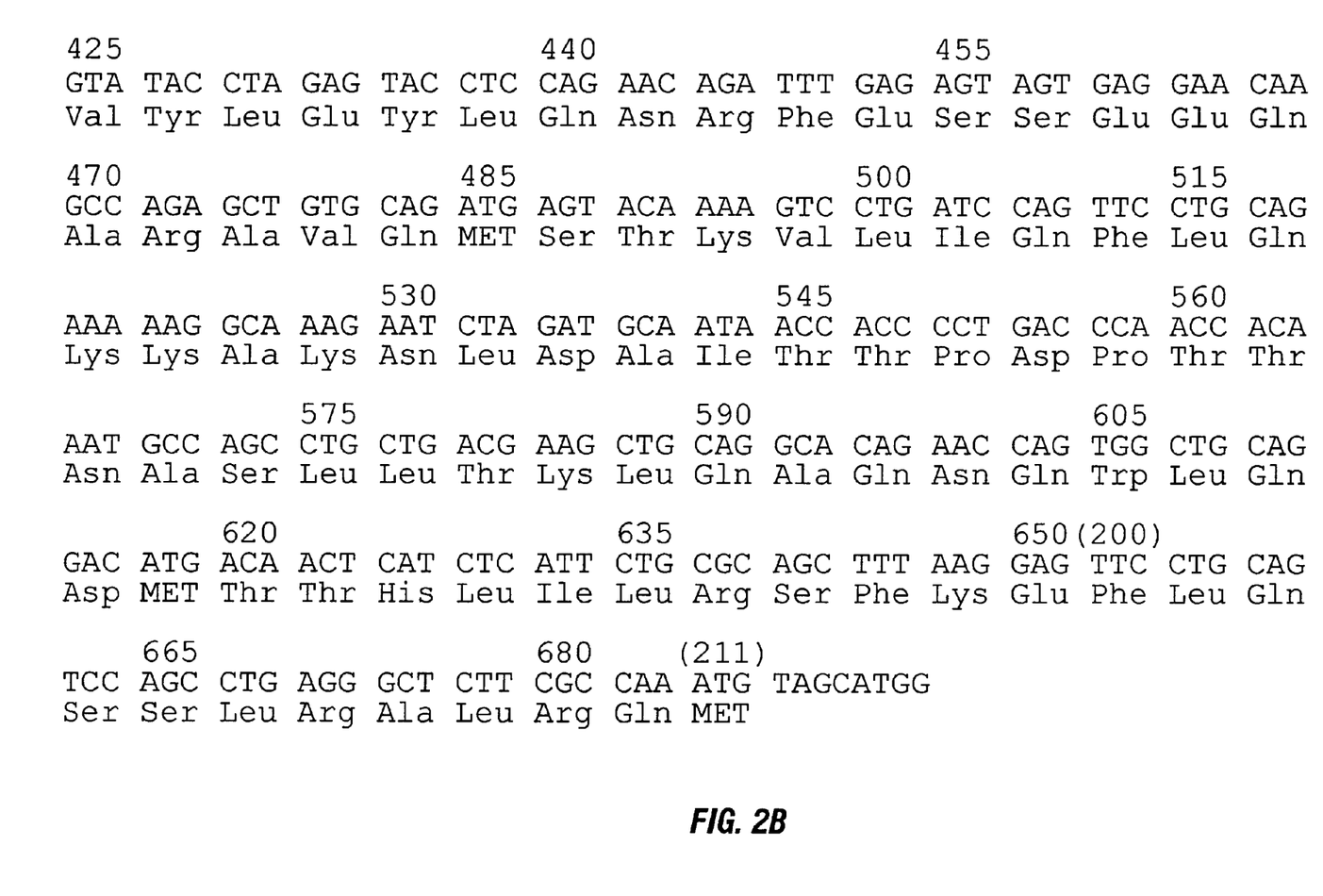
Figure 3:
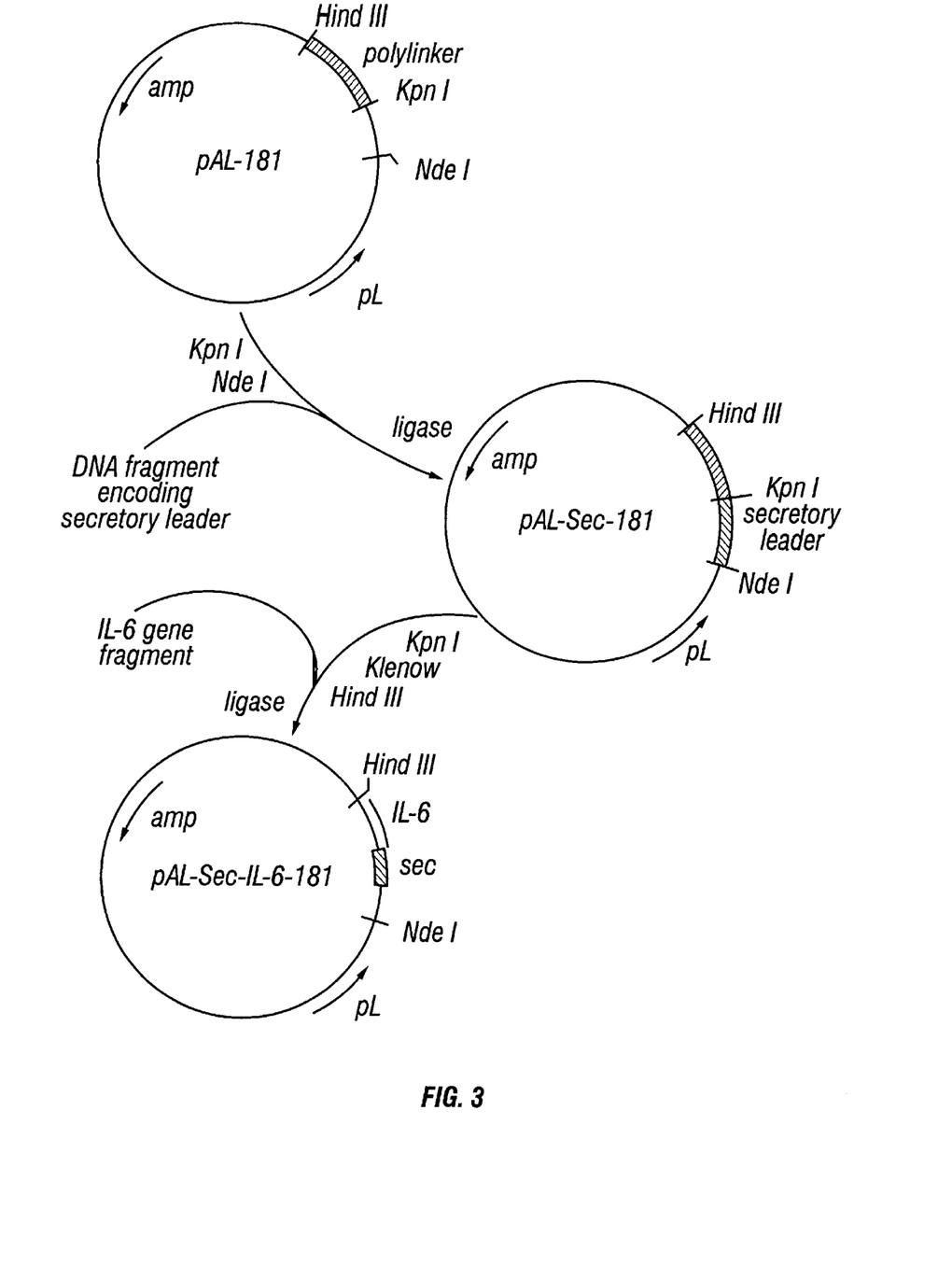
FIG. 3 illustrates the construction of plasmid pAL-Sec-IL6-181.

A preferred embodiment of a DNA sequence encoding IL-6 for use in this method is the sequence of FIG. 2, which has been deliberately designed for expression in bacterial cells. Allelic variants (i.e., naturally occurring base changes in the sequence which occur within a species which may or may not alter the amino acid sequence) of the nucleotide and corresponding peptide sequences of FIGS. 1 and 2 and variations in the nucleotide sequence resulting from the degeneracy of the genetic code are also encompassed for use in the invention where they encode a polypeptide having IL-6 activity.

Variations in the 1.1 kb sequence of FIG. 1 which are caused by point mutations or by induced modifications to enhance the activity or production of the protein should not change the functional protein for which the sequence codes on expression. Therefore, such variations in sequence are encompassed in the invention. For example, the modified sequence of FIG. 2 is presently preferred for expression in bacterial host cells. Such nucleotide modifications deliberately engineered into the DNA sequence or engineered into a sequence produced synthetically by known methods can be made by one skilled in the art using known techniques. Such modification can cause the deletion, insertion or substitution of amino acids in the peptide sequence of IL-6. For example, the replacement of one or more of the cysteine residues in the coding sequence can eliminate a corresponding disulfide bridge. Additionally, the substitution, insertion or deletion of an amino acid at one or more of the tripeptide asparagine-linked glycosylation recognition sites can result in non-glycosylation at that site. Mutagenic techniques for such replacement or deletion are well known to one skilled in the art. [See, U.S. Pat. No. 4,518,584].

The method of the invention involves culturing a suitable cell or cell line which has been transformed with a cDNA sequence which encodes for IL-6, including modified sequences as described above and as represented in FIGS. 1 and 2. The DNA sequence encoding IL-6 in the transformed cell is in operative association with a suitable expression control sequence.

The selection of suitable host cells and methods for transformation, culture, amplification, screening and product production and purification are known in the art. See, e.g. Gething and Sambrook, *Nature*, 293:620–625 (1981), or alternatively, Kaufman et al, *Mol. Cell. Biol.*, 5(7): 1750–1759 (1985) or Howley et al, U.S. Pat. No. 4,419,446.

Bacterial cells are the presently preferred embodiment for host cells in the preparative method of producing IL-6. Bacterial production results in large quantities of active non-glycosylated IL-6. The presently preferred IL-6 sequence for bacterial expression of the protein is the modified sequence of FIG. 2. When IL-6 is expressed in bacterial cells, it may be expressed intracellularly and refolded into active form or it may be secreted from bacterial cells in active form. Various strains of *E. coli*, well-known as host cells in the field of biotechnology [e.g., strain MC1061 and strains described in the examples] are desirably used as host cells which enable the production of biologically active IL-6. A non-exclusive list of various bacterial strains suitable for IL-6 expression include *B. subtilis*, various strains of Pseudomonas, other *bacilli* and the like.

Mammalian cells may also be employed as host cells for production of IL-6. One particularly suitable mammalian cell line is the Chinese hamster ovary [CHO] cell line. Another suitable mammalian cell line, which is described in the accompanying examples, is the monkey COS-1 cell line. A similarly useful mammalian cell line is the CV-1 cell line.

Many strains of yeast cells known to those skilled in the art are also available as host cells for expression of IL-6. Additionally, where desired, insect cells may be utilized as host cells in the method of the present invention. See, e.g. Miller et al, *Genetic Engineering*, 8:277–298 (Plenum Press 1986) and references cited therein.

The present invention also provides vectors and DNA sequences for use in the method of expression of IL-6 protein. The vectors contain the same, or substantially the same, nucleotide sequences as recited above. Preferably the vectors contain the full DNA sequence recited in FIG. 1 or FIG. 2. The vectors also contain appropriate expression control sequences permitting expression of the IL-6 DNA sequence. Alternatively, vectors incorporating modified or naturally occurring allelic sequences as described herein are also embodiments of the present invention and useful in the production of IL-6. The vector may be employed in the method of transforming cell lines and may contain selected regulatory sequences in operative association with the above-described IL-6 DNA coding sequences which are capable of directing the replication and expression thereof in selected host cells. Useful regulatory sequences for such vectors are known to one of skill in the art and may be selected depending upon the selected host cells. Such selection is routine and not considered part of the present invention. Preferred vectors are bacterial vectors.

The protein IL-6 is itself another aspect of the invention. The protein IL-6 is provided substantially free from association with other human proteins due to the provision of its peptide and nucleotide sequences, which enable the synthesis of the peptide by conventional genetic engineering means or the production thereof in recombinant microorganisms. A desirable embodiment of the protein IL-6 is non-glycosylated IL-6, which may be produced by bacterial expression of the gene. IL-6 is characterized by a peptide sequence containing the same or substantially the same peptide sequence as amino acid #28 through amino acid #212, depicted in FIG. 1. IL-6 as produced by the method of the present invention, is characterized by an apparent molecular weight of approximately 20 to 35 kd when analyzed by polyacrylamide SDS gel electrophoresis under nonreducing conditions. In pCSF309 conditioned media, the protein causes the formation of small granulocytic-type colonies in in vitro mouse bone marrow assays at 10 to 100 picomolar concentrations.

FIG. 1 depicts the complete 1.1 kb DNA sequence which encodes for the IL-6 protein and enables expression in appropriate host cells. This sequence contains a long open translational reading frame of 636 nucleotides, encoding a 212 amino acid polypeptide, including an approximately 50 nucleotide conventional leader secretory sequence. The protein coding region of the 1.1 kb sequence extends from nucleotide #132 (the guanine in the alanine codon, amino acid position #28) to nucleotide #686 which is followed by a TAG stop codon. There are two potential asparagine-linked glycosylation sites illustrated by the characteristic sequence, Asn-X-Ser, which may be glycosylated upon expression of the gene in mammalian expression systems. The coding region also contains four cysteines, suggesting two disulfide bonds. The remaining 453 nucleotides of the 3' non-coding sequence of the 1.1 kb region may have a regulatory role in transcription in the natural host. The 3' end of the sequence also contains an AT-rich segment including several repeats of the sequence ATTTA, which is believed to be related to the RNA message stability [See, G. Shaw and R. Kamen, *Cell,* 46(5):659–677 (1986)].

The preferred sequence for bacterial expression shown in FIG. 2 has the same peptide sequence of FIG. 1, but has a selectively modified nucleotide sequence to enhance the production of IL-6 in bacterial expression systems. Additionally, this preferred sequence has deleted much of the leader sequence and 3' non-coding sequence present in FIG. 1.

One preferred embodiment of the present invention is bacterially produced non-glycosylated IL-6. When produced in bacterial cells the alanine at position 28 of the protein coding sequence is generally clipped off by bacterial enzymes. Therefore, approximately 80% of the bacterially produced IL-6 protein has proline, position 29, as its 5' initial amino acid. Bacterially produced IL-6 is non-glycosylated and consequently, has a more homogeneous apparent molecular weight than IL-6 produced in other expression systems. Additionally, when encoded by the DNA sequence of FIG. 2, bacterially produced IL-6 is produced in high yields.

Methods and therapeutic compositions may employ IL-6 as at least one active ingredient. IL-6 may be used, alone or in co-administration with other therapeutic products, in the treatment of diseases characterized by a decreased level of either myeloid or lymphoid cells of the hematopoietic system or combinations thereof. This protein may also be capable of stimulating accessory and mature cells, e.g. monocytes, to produce other hematopoietic-like factors which, in turn, stimulate the formation of colonies of other hematopoietic cells, as well as other hematopoietic-like activities. Alternatively, IL-6 may enhance the activity of other hematopoietins. For example, IL-6 has demonstrated the ability in a 5-fluorouracil-treated mouse bone marrow assay to enhance the ability of other hematopoietins, namely IL-3 and CSF-1, to stimulate the proliferation of hematopoietic cells more primitive than those induced by CSF-1 or IL-3 alone. This characteristic has previously been attributed to a protein called IL-1-alpha or Hematopoietin 1, which may induce expression of IL-6. Similarly in a human blast cell assay IL-6 and IL-3 in combination caused the proliferation of early human stem cell colonies. Thus IL-6 has potential pharmaceutical use in combination with IL-3 in the treatment of many disease states which involve immune system deficiencies, for example, in treating persons suffering from over-exposure to radioactivity or chemotherapy.

Various immunodeficiencies e.g., in T and/or B lymphocytes, or immune disorders, e.g., rheumatoid arthritis, may also be beneficially effected by treatment with IL-6. Immunodeficiencies, such as leukopenia, a reduction in the number of circulating leukocytes in the peripheral blood, may be the result of viral infections, e.g., HTLVI, HTLVII, HIV, severe exposure to radiation, side effects of cancer therapy or the result of other medical treatment. Therapeutic treatment of leukopenia with IL-6 compositions may avoid undesirable side effects caused by treatment with presently available drugs. Other conditions susceptible for IL-6 treatment include patients recovering from bone marrow transplants.

Compositions for use in treating the above-described conditions comprise a therapeutically effective amount of IL-6 in admixture with a pharmaceutically acceptable carrier. This composition can be systematically administered either parenterally, intravenously or subcutaneously. When systematically administered, the therapeutic composition for use in this invention is, of course, in the form of a pyrogen-free, parenterally acceptable aqueous solution. The preparation of such a parenterally acceptable protein solution, having due regard to pH, isotonicity, stability and the like, is within the skill of the art.

The dosage regimen involved in a method for treating the above-described conditions will be determined by the attending physician considering various factors which modify the action of drugs, e.g. the condition, body weight, sex and diet of the patient, the severity of any infection, time of administration and other clinical factors. Generally, the daily regimen should be in the range of 200–1000 micrograms of polypeptide or 50 to 5000 units (ie, a unit being the concentration of polypeptide which leads to half maximal stimulation in a standard murine bone marrow assay) of polypeptide per kilogram of body weight.

As one preferred embodiment, IL-6 is employed in combination with other agents, to activate mature lymphoid cells. Specifically, it has been found that IL-6 has CDF activity in a published assay [Y. Takai et al, *J. Immunol.,* 137(11):3494–3500 (1986)]. Thus, IL-6 in combination with IL-2 alone and in combination with IL-2 and gamma interferon activates mature lymphoid cells. This particular combination may be used in anti-cancer and anti-viral therapeutic treatments. [See also, Takai et al., *Science* (1986) in press]. This utility is attributed in part to the cytolytic T cell activity demonstrated by IL-6. It is thus expected that simultaneous or serial treatment of a patient with IL-6 and IL-2 and gamma interferon may be efficacious particularly in the treatment of metastatic cancers. Similarly, IL-6 may be employed in combination with IL-2 for LAK therapy.

A non-exclusive list of other appropriate hematopoietins, CSFs and interleukins for simultaneous or serial co-administration with IL-6 includes GM-CSF, CSF-1, G-CSF, Meg-CSF, erythropoietin (EPO), IL-1, IL-3, B-cell growth factor and eosinophil differentiation factor. Such combinations may enhance the activity or effect of treatment with the other hematopoietins alone.

IL-6 may also augment the humoral or cellular immune response in vivo in co-administration with other therapeutic agents. For example, IL-6 may enhance the efficacy of viral antigen vaccines, such as HIV and the like, or tumor antigen vaccines.

The dosage of IL-6 in these co-administration regimes would be adjusted from the dosages recited for administration of IL-6 alone to compensate for the additional components, e.g. IL-2, in the therapeutic composition. Progress of the treated patient can be monitored by periodic assessment of the hematological profile, e.g., white cell count and the like.

IL-6 may also be employed in well-known procedures to generate polyclonal and monoclonal antibodies, both human and murine, for diagnostic and therapeutic use. Such monoclonal or polyclonal antibodies may be used therapeutically by attachment to targeting or toxin agents, labels and the like. IL-6 also functions as a hybridoma growth factor in the culture medium for hybridoma cell lines to increase the yields thereof.

The following examples illustrate the method of the present invention employing cDNA sequences encoding IL-6. The complete DNA sequence of FIG. 1 was isolated from poly A+ mRNA library of the HTLV I transformed human T-cell line C10MJ2 [National Institute of Health; S., K. Arya et al, *Science,* 223:1086 (1984)] employing the expression cloning technique described in U.S. Pat. No. 4,675,285.

EXAMPLE I

Construction of an exemplary bacterial expression vector for intracellular expression The sequence of FIG. 1 contained in pCSF309 (ATCC 67153) as an EcoRI insert [see Example III], may be excised therefrom by digestion with EcoRI and inserted into a suitable bacterial vector and host for the production of IL-6. However, a preferred bacterial expression system for IL-6 which provides for higher yields of the protein by altering the 5' coding sequence of IL-6 employs the sequence of FIG. 2.

This preferred sequence was used to construct bacterial expression plasmid pAL309C-781 as follows:

The cDNA clone of IL-6 [FIG. 1], carried on an EcoRI fragment, was transferred into M13mp19 [See, S. Messing, *Methods in Enzymology,* 101:20–78 (1983); J. Norrander et al., *Gene,* 26:101–106 (1983)] in such an orientation that the noncoding strand was packaged into phage. Single-stranded phage DNA was prepared and annealed with the oligonucleotide d(GCCCCAGTACCCCCAGGAGAAG). The oligonucleotide was extended with Klenow fragment of DNA polymerase I of *E. coli;* and the residual single-stranded region was digested with S1 nuclease. The ends were made blunt by treatment once again with Klenow fragment of DNA polymerase; and finally the double-stranded IL-6 cDNA was prepared by digestion with HindIII. The blunt end to HindIII fragment was ligated into pAL-181 (ATCC #40134) which had been digested with KpnI, treated with Klenow fragment of DNA polymerase and digested with HindIII.

The resultant plasmid pAL309-181 was modified first by removing the base sequence fragment between bp #149 to 169 of FIG. 1 by in vitro site-directed loop-out mutagenesis. [See, Morinaga, et al., *Biotechnology* 2:636–639 (1984)]. This deletion created a unique NarI site in the IL-6 sequence. This plasmid was digested with NarI. The single-stranded ends were filled in with Klenow fragment of DNA polymerase I; and then digested with HindIII. The fragment from this digest carrying the 3'-end of the IL-6 gene was isolated. This fragment was mixed with a 42 bp synthetic duplex of DNA which was made to be blunt on one end and carry a 5'-single-stranded TA sequence on the other. The mixture was ligated with pAL181 cut with NdeI and HindIII. This three-way ligation produced the modified IL-6 gene sequence shown in FIG. 2 and an expression plasmid called pAL309B-181.

Plasmid pAL309B-181 was cut with BanI and the single-stranded end filled in using Klenow fragment of DNA polymerase I. The plasmid was then cut with NdeI and the IL-6 clone isolated. This DNA fragment was inserted between the NdeI and a filled in XbaI site of a pAL-181 vector into which a synthesis DNA sequence carrying the putative transcriptional termination sequence found 3' to the end of the *E. coli* aspA coding sequence had been cloned previously.

This new plasmid, called pAL309C-781, can be transformed by conventional techniques into a suitable bacterial host cell which contains means for controlling the PL promoter {see, e.g. Example V} for expression of the IL-6 protein.

Alternatively, the modified IL-6 coding sequence could be removed from pAL309C-781 by excision with Nde I and Hind III or from pCSF309 by excision with Eco RI and inserted into any desired bacterial vector using procedures and vectors such as described in T. Maniatis et al, *Molecular Cloning A Laboratory Manual,* Cold Spring Harbor Laboratory (1982). These exemplary bacterial vectors could then be transformed into bacterial host cells and IL-6 expressed thereby.

EXAMPLE II

Construction of exemplary bacterial expression vectors for extracellular secretion and expression IL-6 can be produced by secretion of the protein into the periplasm of *E. coli*. This produces a fully oxidized, non-glycosylated protein having a high specific activity in in vitro bioassays. Two exemplary vectors for production of IL-6 by secretion from bacteria are described.

(1) Plasmid pUC18 [Yanisch-Perron et al., Gene 33:103 (1985)] was cut with restriction endonuclease NdeI, the resultant sticky ends made blunt by treating them with Klenow fragment of *E. coli* DNA polymerase I and deoxynucleoside triphosphates, and the plasmid recircularized with T4-DNA ligase. The resultant plasmid #1 was then cut with both PvuII (partial digestion) and EcoRI and the ends made blunt by the action of Klenow fragment of DNA polymerase. The appropriate fragments were purified and religated to produce a plasmid #2 in which the EcoRI to PvuII fragment containing the lac promoter had been removed. Plasmid #2 was digested with EcoRI and treated with S1 nuclease to remove the single-strand ends. The plasmid was then cut with KpnI.

Plasmid pAS1 [Rosenberg, Ho and Shatzman, *Meth. Enzymol.,* 101:123(1983)] was cut with BamH1 and the single-strand ends removed by digestion with S1 nuclease. A linker with the sequence d(GTACCCGGGTAC) was ligated with this digested pAS1 DNA to give a plasmid pAS2, which has a KpnI site replacing the BamH1 site in pAS1. pAS2 was cut with BglII, the ends made blunt by the action of Klenow fragment of DNA polymerase and the DNA cut with KpnI. The BglII (Blunt) to KpnI fragment containing the pL promoter sequence was ligated with the EcoRI (blunt) to KpnI vector sequence of plasmid #2 to create pAL-181, a plasmid carrying the pL promoter, ribosome binding site, and an ATG initiation codon followed immediately by a KpnI site and the polylinker region of pUC18. Plasmid pAL-181 was deposited with the American Type Culture Collection, 12301 Parklawn Dr., Rockville, Md. on Aug. 28, 1984 under accession number 40134.

Plasmid pAL-181 was cut with NdeI and KpnI and the following synthetic DNA secretion leader sequence was inserted:

```
TATG AAA AAT ATA ACT TTC ATT TTT TTT ATT TTA TTA
 AC TTT TTA TAT TGA AAG TAA AAA AAA TAA AAT AAT
GCA TCG CCA TTA TAT GCGGTAC
CGT AGC GGT AAT ATA CGC
```

This sequence encodes a typical secretory leader sequence. The plasmid resulting from this construction was called pAL-Sec-181.

pAL-Sec-181 was cut with KpnI and treated with Klenow fragment of DNA polymerase to remove the single-strand ends. The plasmid was recut with HindIII and ligated to the IL-6 containing DNA fragment described in Examples I and III. This fragment began with the sequence GCCCCAGTACCCCCAGGAGAAG, which encodes the first alanine codon of mature IL-6, and continued through the entire IL-6 sequence and 3'-untranslated region until it reached the HindIII site within the M13mp19 polylinker. The resultant plasmid, pAL-Sec-IL6-181, encodes a protein, the synthesis of which is controlled by the pL promoter, which is composed of the secretion leader fused to the mature IL-6 protein.

Figure 4:
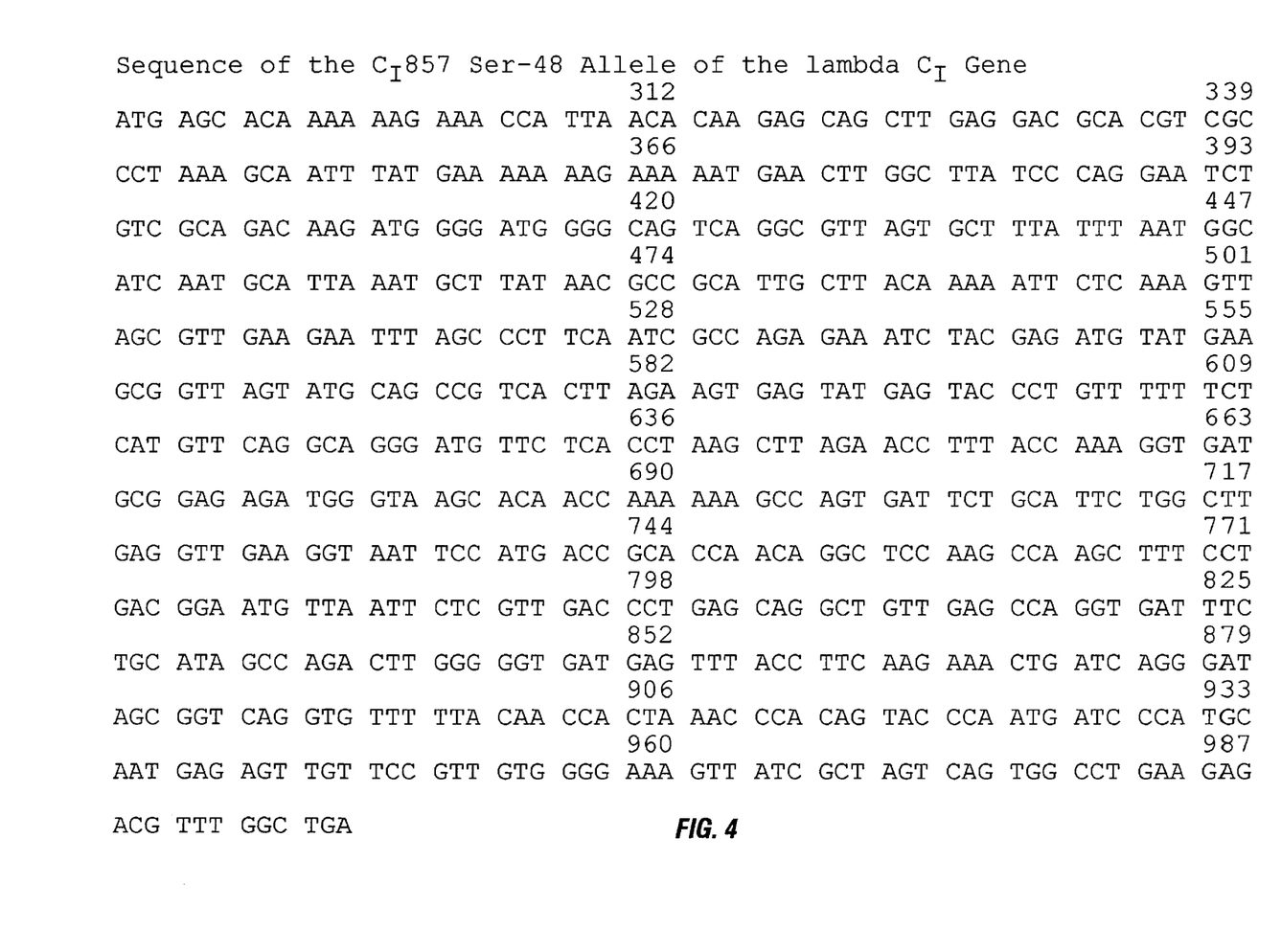
FIG. 4 illustrate the CI allele for the hyper-secreting bacterial expression system.

(2) To obtain a hyper-secreting expression system for bacterially-produced IL-6, the $C_I$, rex and N region of bacteriophage lambda contained in nucleotides 34499 to 38214, as described by F. Sanger et al. *J. Mol. Biol.,* 162:729 (1982) are inserted into the ClaI site of the lacZ gene, which is cloned onto a conventional plasmid. The $C_I$ gene employed was an allele having the sequence shown in FIG. 4. The sequence of this gene was altered by conventional methods so that the glycine at position 48 was changed to serine, i.e., a G to A transition in the first position of the codon. This $C_I$ 857 Ser-48 allele was then inserted into the *E. coli* genome via homologous recombination into the lacZ gene of the cell. Once inserted it yielded a lacZ, lambda immune *E. coli*.

The gene for human IL-6 was fused to a conventional sequence encoding a secretory leader. These sequences were operatively linked to the wild-type pL promoter sequence on a conventional plasmid and transformed into the lambda immune *E. coli* cells carrying $C_{I857}$ Ser-48. The cells with the $C_{I857}$ Ser-48 gene produced a significant amount of the IL-6 protein in active form in the periplasm.

EXAMPLE III
Construction of an exemplary mammalian expression vector pCSF309

To construct a mammalian vector for expression of IL-6 the complete cDNA sequence depicted in FIG. 1 was ligated into EcoRI-digested COS cell expression vector p91023B [which may be obtained by digesting pCSF-1 (ATCC 39754) with EcoRI to remove an approximately 750 base pair insert]. p91023B contains the SV40 enhancer, major adenovirus late promoter, DHFR coding sequence, SV40 late message poly-A addition site and VaI gene. The plasmid resulting from the EcoRI digestion of p91023B and the insertion of the DNA sequence of FIG. 1 encoding for IL-6 was designated pCSF309. pCSF309 (ATCC #67153) can be transformed by conventional techniques into a suitable mammalian host cell for expression of IL-6.

Exemplary host cells for mammalian cell expression include particularly primate cell lines, rodent cell lines and the like, e.g. COS cells.

One skilled in the art can also construct other mammalian expression vectors comparable to pCSF309 but containing less than the entire sequence of FIG. 1. For example, the 5' and 3' flanking sequences may be cut from the sequence of FIG. 1 if desired; or modified or allelic variations of FIG. 1 may be employed by manipulating the sequence thereof. The DNA sequence of FIG. 1 can be cut from the plasmid with EcoRI and well-known recombinant genetic engineering techniques employed to modify the sequence and to insert it into other known vectors, such as pCD [Okayama et al., *Mol. Cell Biol.* 2:161–170 (1982)] and pJL3, pJL4 [Gough et al., *EMBO J.,* 4:645–653 (1985)]. The transformation of these vectors into appropriate host cells can result in expression of IL-6.

EXAMPLE IV
Construction of Yeast or Insect Vectors

In a manner similar to that of Example I, one skilled in the art could manipulate the sequence of FIG. 1 by eliminating or replacing the mammalian regulatory sequences flanking the coding sequence with other expression control sequences to create yeast or other fungal vectors. Thus this sequence would then be expressible in fungal host cells. A non-exclusive list of fungal cells include strains of the genera Sacchromyces, Aspergillus and Pichia, as well as other known strains. For the construction of a yeast vector and expression of the protein in yeast cells, see, e.g. procedures described in published PCT application WO 86 00639.

Insect cells could also be employed as host cells where desired, and the sequence of FIGS. 1 and 2 altered for such an expression system. For example, the coding sequence of FIG. 1 could be cut from pCSF309 with EcoRI and further manipulated (e.g. ligated to other known linkers or modified by deleting non-coding sequences therefrom or altering nucleotides therein by other known techniques). For the construction of an insect vector, see, e.g. procedures described in published European patent application 155,476.

EXAMPLE V
Expression of IL-6 Protein

A. Bacterial Expression—Intracellular

Plasmid pAL309C-781 from Example I was transformed into an *E. coli* K12 strain GI455, a derivative of strain W3110 in which the $C_I$ and Rex regions of bacteriophage lambda carrying the $C_{I857}$ allele have been inserted into the ClaI site of the lacZ gene of the bacterial genome. This insert consists of all of the DNA sequences between nucleotides 35711 and 38104 of the phage genome [See, F. Sanger et al. *J. Mol. Biol.* 162:729 (1982)].

When GI455 transformed with pAL309C-781 is grown at 30° C. to high cell density and then heated to 40° C., IL-6 is produced rapidly and accumulates over the next two or three hours to reach greater than 10 percent of the total cellular protein. This protein is produced in an insoluble form which must be solubilized and refolded by conventional methods. [See, e.g., T. E. Creighton, *Prog. Biophys. Molec. Biol.,* 33:231–297 (1978)]. This bacterially produced IL-6 is predicted to have a specific activity in the murine bone marrow assay of between approximately $10^6$ to $2 \times 10^7$ units per mg protein.

B. Bacterial Secretion

Plasmid pAL-Sec-IL6-181 from Example II was transformed into *E. coli* K-12 strain GI400. This strain is a derivative of W3110 [Bachmann, *Bacterial. Rev.,* 36 525 (1972)] in which the $C_I$, Rex and N regions of bacteriophage lambda (nucleotides 33498 to 38214 of the phage genome) [Sanger et al., *J. Mol. Biol.,* 162:729(1982)] has been inserted into the ClaI site of the lacZ gene of the bacterium. The $C_I$ gene on this insert is the temperature-sensitive $C_{I857}$ allele.

Once pAL-Sec-IL6-181 was transformed into GI400, the cells could be grown at 30° C. to a desirable cell density and the temperature increased to 40° C. to initiate secretion of IL-6. The product isolated from the periplasm of these cells was homogeneous in molecular weight. The processing event removes the leader sequence. The N-terminal alanine was also removed from the secreted protein, producing a product with proline as its N-terminal amino acid in the majority of cases. The material has a high specific activity on a bone marrow colony assay showing from $1-20 \times 10^6$ units/mg protein.

C. Mammalian Expression

Plasmid DNA, prepared from *E. coli* MC1061 containing pCSF309 as described in Maniatis et al., supra was purified by conventional methods involving equilibrium centrifugation in cesium chloride gradients containing ethidium bromide. COS cells (ATCC CRL 1650) were transfected with the purified DNA at a concentration of approximately 5 µg plasmid DNA per $10^6$ COS cells and treated with chloroquine according to the procedures described in G. G. Wong et al., *Science,* 280:810–815 (1985) and R. J. Kaufman et al. *Mol. Cell Biol.,* 2:1304 (1982). 72 hours following transfection pCSF309-containing COS cell conditioned medium can be harvested containing a protein which demonstrates activity in standard murine bone marrow assay, as described in Example V.

EXAMPLE VI
IL-6 Activity in In Vitro Mouse Bone Marrow Assays

Mouse bone marrow assays were conducted as described in D. Metcalf, *The Hemopoietic Colony Stimulating Factors*, Elsevier Press, New York (1984) with the following modifications:

(a) $2 \times 10^5$ bone marrow cells per ml were employed in the assay;

(b) final assay volume was 100 µl; and (c) assays were set up in standard 96 well microtitre plates.

Bone marrow was obtained from the femurs of 6–25 week old female Balb/c mice (Jackson). Using WEHI 3 conditioned medium [J. C. Lee et al., *J. Immunol.*, 128:2393–2398 (1982)] which contains mouse interleukin-3 as a standard control, one dilution unit of activity was defined as that concentration of protein which results in a maximal response in this bone marrow assay, i.e. approximately 25 to 35 colonies per $2 \times 10^4$ mouse bone marrow cells.

Conditioned medium from COS cells containing pCSF309 was found to be active to at least $10^{-4}$ dilution in a mouse bone marrow assay and produced small granulocytic type colonies. The number and type of cells in a maximal response will vary with the strain and age of the mouse donors.

Conditioned medium from *E. coli* cells containing pAL309C-781 may have a specific activity at least $10^6$ to $2 \times 10^7$ units per mg protein in this assay. Bacterially produced IL-6 also produced granulocytic colonies.

EXAMPLE VII
Molecular Weight Analysis of IL-6

Following the procedure of R. J. Kaufman and P. A. Sharp, *J. Mol. Biol.*, 159:601–629 (1982), $^{35}$S methionine can be metabolically incorporated into the IL-6 protein made by COS cell transfection with pCSF309 DNA. When $^{35}$S methionine labelled pCSF309-containing COS cell conditioned medium is analyzed under non-reducing conditions by SDS polyacrylamide gel electrophoresis, [U. K. Laemmli, *Nature*, 227:680–685 (1970)] a broad band, indicative of glycosylation, can be detected at an apparent molecular weight of approximately 20 to 35 kd.

EXAMPLE VIII
Construction of CHO cell lines expressing high levels of IL-6

One method for producing high levels of IL-6 from mammalian cells involves the construction of cells containing multiple copies of the heterologous IL-6 gene. The heterologous gene can be linked to an amplifiable marker, e.g. the dihydrofolate reductase (DHFR) gene for which cells containing increased gene copies can be selected for by propagation in increasing concentrations of methotrexate (MTX) according to the procedures of Kaufman & Sharp, *J. Mol. Biol.*, supra. This approach can be employed with a number of different cell types. pCSF309 and the DHFR expression plasmid pAdA26SV-(A)3 (Kaufman & Sharp, *Mol. Cell Biol.*, supra) are co-transfected into DHFR-deficient CHO cells, DUKX-BII, by calcium phosphate coprecipitation and transfection. The initial DHFR expressing transformants are selected for growth in alpha media with dialyzed fetal calf serum, and subsequently selected for amplification by growth in increasing concentrations of MTX (sequential steps in 0.02, 0.2, 1.0 and 5 mM MTX) as described in Kaufman, et al., *Mol. Cell Biol.*, 5:1750 (1983). Transformants are cloned, and biologically active IL-6 protein expression is monitored by murine bone marrow assays. IL-6 expression should increase with increasing levels of MTX resistance.

Numerous modifications and variations in practice of this invention are expected to occur to those skilled in the art upon consideration of the foregoing descriptions of preferred embodiments thereof. Such modifications and variations are believed to be encompassed in the appended claims.

What is claimed is:

1. A method for stimulating growth of hematopoietic cells in a patient suffering from an immune system deficiency resulting from exposure to radiation, which comprises administering an effective amount of a protein selected from the group consisting of a protein having the amino acid sequence set forth in FIG. 1, said protein being produced in mammalian cells containing the DNA sequence set forth in FIG. 1; a protein having the amino acid sequence set forth in FIG. 1 from amino acid 28 to amino acid 212; and a non-glycosylated protein having the amino acid sequence set forth in FIG. 2 from amino acid 29 to amino acid 212.

2. The method according to claim 1, wherein the protein has the amino acid sequence set forth in FIG. 1 and is produced in mammalian cells containing the DNA sequence set forth in FIG. 1.

3. The method according to claim 1, wherein the protein is characterized by the amino acid sequence set forth in FIG. 1 from amino acid 28 to amino acid 212.

4. The method according to claim 1, wherein the protein is non-glycosylated and is characterized by the amino acid sequence set forth in FIG. 2 from amino acid 29 to amino acid 212.

5. A method for stimulating growth of hematopoietic cells in a patient suffering from an immune system deficiency resulting from exposure to chemotherapy, which comprises administering an effective amount of a protein selected from the group consisting of a protein having the amino acid sequence set forth in FIG. 1, said protein being produced in mammalian cells containing the DNA sequence set forth in FIG. 1; a protein having the amino acid sequence set forth in FIG. 1 from amino acid 28 to amino acid 212; and a non-glycosylated protein having the amino acid sequence set forth in FIG. 2 from amino acid 29 to amino acid 212.

6. The method according to claim 5, wherein the protein has the amino acid sequence set forth in FIG. 1 and is produced in mammalian cells containing the DNA sequence set forth in FIG. 1.

7. The method according to claim 5, wherein the protein is characterized by the amino acid sequence set forth in FIG. 1 from amino acid 28 to amino acid 212.

8. The method according to claim 5, wherein the protein is non-glycosylated and is characterized by the amino acid sequence set forth in FIG. 2 from amino acid 29 to amino acid 212.

* * * * *